United States Patent
Sullivan et al.

(10) Patent No.: US 6,455,719 B1
(45) Date of Patent: *Sep. 24, 2002

(54) CONSTRAINED GEOMETRY LIGANDS AND COMPLEXES DERIVED THEREFROM

(75) Inventors: Jeffrey M. Sullivan, Loveland; Daniel A. Gately, Berthoud, both of CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/761,151

(22) Filed: Jan. 17, 2001

(51) Int. Cl.$^7$ .............................. C07F 17/00; C07F 7/28
(52) U.S. Cl. ........................ 556/11; 556/12; 526/160; 526/943; 502/103; 502/117
(58) Field of Search ................... 556/11, 12; 502/103, 502/117; 526/160, 943

(56) References Cited

U.S. PATENT DOCUMENTS 6,015,916 A  *  1/2000  Sullivan et al. ................ 556/7

* cited by examiner

Primary Examiner—Porfirio Nazario-Gonzalez
(74) Attorney, Agent, or Firm—Edward S. Irons

(57) ABSTRACT

A novel constrained geometry titanium(II) diene complex and ligands of such complexes are described. The novel complex has an olefin polymerization activity substantially in excess of a defined activity standard characteristic of analogous prior art constrained geometry diene complexes. Methods for the synthesis of the novel, high-activity complexes are described.

1 Claim, No Drawings

CONSTRAINED GEOMETRY LIGANDS AND COMPLEXES DERIVED THEREFROM

FIELD OF THE INVENTION

This invention relates to constrained geometry complexes of group 4 metals and dienes characterized by high olefin polymerization activity, to ligands of such complexes and to methods for the production of such complexes and ligands.

BACKGROUND OF THE INVENTION

U.S. Pat. No. 5,470,993 describes the synthesis of constrained geometry group 4 metal diene complexes by contacting a reduced form of a group 4 metal tetrjhalide, a diene and an appropriate dianion ligand of the desired metal complex.

The diene complexes may have the formula which appears at lines 20–34 of Column 5 of U.S. Pat. No. 6,015,916 as follows:

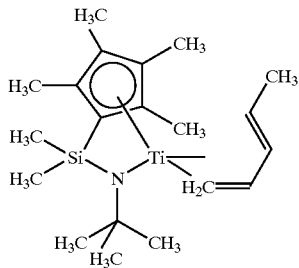

The corresponding dihalo ligand may have the formula also set forth in U.S. Pat. No. 6,015,916 (see Formula II of claim 1):

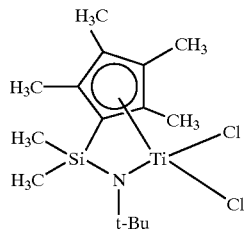

The ligand may be any corresponding dihalo compound in which the chlorine substituents are replaced by bromine, iodine or fluorine and in which the "t-bu" substituent is replaced by any alkyl group.

U.S. Pat. No. 6,015,916 describes the synthesis of similar complexes by treatment of a dihalo ligand of a metallocene compound with an alkali metal alkyl and a diene. The specification of U.S. Pat. No. 6,015,916 is, by express reference, incorporated herein and made a part of this specification.

German Application DE 197 39 946 A1 describes a metallocene synthesis in which an appropriate ligand is converted to a metallocene by treatment with an adduct of Formula (I)

$$M^1X_nD_a \qquad (I)$$

in which $M^1$ denotes a metal of groups 3, 4, 5 or 6 or the periodic system of elements (PSE) or an element of the group of lanthanides or actinides, preferably titanium, zirconium, or hafnium, by special preference zirconium; X is the same or different, being halogen, a $C_{1-10}$-alkoxy, $C_{6-10}$-aryloxy, $C_{1-10}$-alkylsulfonate such as mnesylate, triflate, nonaflate, a $C_{6-10}$-arylsulfonate such as tosylate, benzene sulfonate, a $C_{1-10}$-alkylcarboxylate such as acetate, formate, oxalate, or a 1,3-dlcarbonylate such as acetylacetonate or a fluorinated 1,3-dicarbonylate; n is an integer and equals 2, 3, 4, 5 or 6 and corresponds to the oxidation number of the metal $M^1$; a is an integer or a fraction number and $0<a \leq 4$; and D is a linear, cyclic, or branched oligoether or polyether containing at least two oxygen atoms or an oligoether or polyether containing at least two sulfur atoms.

There is a need for group 4(II) diene complexes of high catalytic activity in which these disadvantages are reduced or eliminated and for dihalo ligands of such complexes.

Accordingly, it is an object of this invention to provide novel cyclopentadienyl group 4 metal diene complexes and dihalo ligands or such complexes which provide uniquely active olefil polymerization catalysts.

It is a related object of the invention to provide cyclopentadienyl group 4 metal diene complex single site polymerization catalysts and catalyst compositions of low impurity content such that the single site functionality thereof is not significantly impaired.

It is a specific object of the invention to provide a magnesium-free cyclopentadienyl group 4 metal diene complex metallocene.

DEFINITIONS

The following expressions have the meaning set forth:

(1) Cyclopentadienyl group means cyclopentadienyl, tetraalkylcyclopentadienyl, indenyl, tetrahydroindenyl, fluorenyl, tetrahydrofluorenyl, or octahydrofluorenyl.

(2) The expressions group 4(II) and group 4(III) mean a group 4 metal of valence 2(II) or 3(III).

(3) A Group 4(II) metallocene compound is a compound comprised of a group 4(II) metal bonded to one or more cyclopontadienyl groups.

(4) A Group 4(II) metallocene ligand is a chemical precursor which contains a cyclopentadienyl or substituted cyclopentadienyl group from which a group 4(II) metllocene may be synthesized.

(5) Constrained geometry compound or catalyst (CGC) means a catalyst in which the metal center is contained in a ring structure and covalently bonded to a cyclic group via a delocalized n-system and covalently bonded via a sigma-bond to another atom, e.g., carbon, nitrogen, oxygen. A small ring size induces constraint about the metal atom center. For titanium-containing CGCs, the incorporated titanium atom can be in the +4, +3, or +2 formal oxidation state. See EP application 90309496.9, WO 95/00526 and U.S. Pat. No. 5,470,993.

(6) CpSA ligand means (t-butylamino) (tetramethylcyclopentadienyl) dimethylsilane.

(7) $(CpSA)^{2-}$ means doubly-deprotonated CPSA ligand.

(8) $(CpSA)^{2-}TiCl_2$ means [(t-butylarido) (tetramethylcyclopentadienyl)dimethylsilane] titanium dichloride.

(9) Activity means generally the quantity of polymer produced under standard conditions by a defined amount of catalyst per unit time.

CATALYTIC ACTIVITY DETERMINATION

As used in this application, catalyst efficiency or activity is based on ethylene consumption in a batch reactor under standard conditions for temperature, solvent, monomer quantities, hydrogen quantities, monomer pressure and run time.

The activity of the sample catalyst is reported as the percentage of activity of the sample versus the activity of a standard ("standard activity"). For purposes of this application, the "standard" is the CGC group 4(II) diene complex from Boulder Scientific Company Batch 459-0140 of 1997.

The equation for reporting the sample catalyst activity is as follows:

$$\% \text{ Activity} = \frac{\text{Average Sample Activity}}{\text{Average Standard Activity}} \times 100 = \text{Sample Activity}$$

"Average" means the average of two runs with activities which are the same within plus or minus 5%

"PROCESS DESCRIPTION" AND "REACTION" FOR "STANDARD" CGC BSC-1459-4-0140 DATED FEB. 26, 1997

PROCESS DESCRIPTION

This process involves making reactant slurries 1 and 2 in separate vessels and then combining these slurries for the final reaction. Slurry 1 is produced by charging toluene into a vessel and deoxygenating. Then titanium tetrachloride is added, followed by adding n-butyllithium. This addition is very exothermic. The resulting mixture comprising slurry 1 is stirred for 1 hour. This process is illustrated by equation 1):

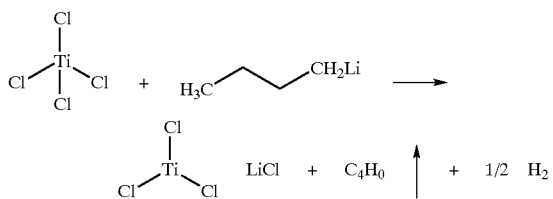

Slurry 2 is made up as follows: Toluene and CpSA ligand are charged to a reaction vessel. After adjusting the pot temperature to 45–50° C., a solution of isopropylmagnesium chloride in ethyl ether is fed into the reaction vessel resulting in gas evolution. Gentle heating is used as needed in order to end up with a pot temperature of 45–50° C. at the end of the Grignard feed. The reaction mixture is slowly heated and solvents begin to distill along with increased gas evolution. The reaction mixture is heated up to 85–90° C., and this temperature is maintained for 2 hours. After allowing the reaction mixture to cool to 60–65° C., TiCl₃ is fed into the reaction vessel. The reaction mixture is then cooled to 20–25° C. This becomes known as Slurry 2. This process is illustrated by equations 2) and 3):

2)
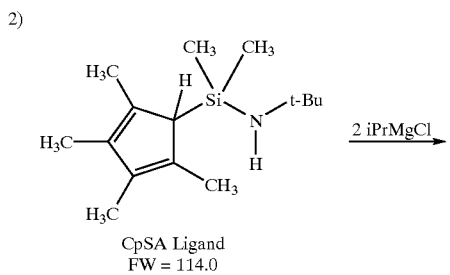
CpSA Ligand
FW = 114.0

3)
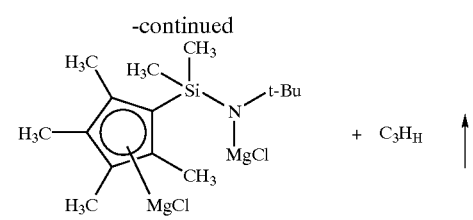

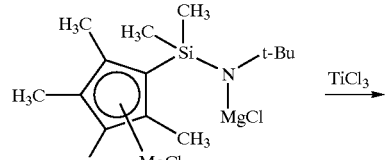

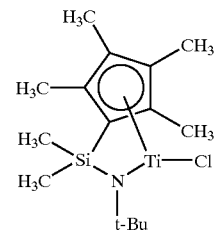

The agitated Slurry 1 is transferred into the reactor containing the agitated Slurry 2 as quickly as possible resulting in about a temperature increase of about 7–15° C. Methylene chloride is then charged to the reaction vessel, the vessel containing Slurry 1 is then rinsed out with toluene and charged to the Slurry 2 reaction vessel, and this mixture is then agitated for 2 hours. A dark reddish-brown color is noted in the reaction vessel as soon as Slurry 1 is introduced. This reaction is illustrated by equation 4):

4)
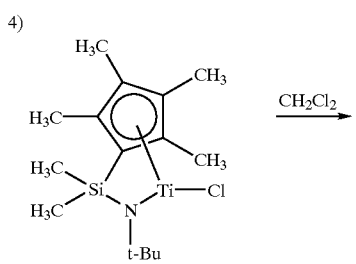

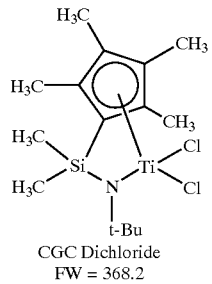
CGC Dichloride
FW = 368.2

Solvents are removed under reduced pressure (60–80 mm Hg) using a rotary vane vacuum pump to about ½ of the starting volume. Toluene is added back, Celite is added, and the mixture is filtered through the large Sparkler filter.

Solvents are then distilled to concentrate the product. The remaining crude product solution is then used directly in the next step.

"PROCESS DESCRIPTION" AND "REACTION" FOR CONVERSION OF CGC DICHLORIDE TO A GROUP 4(II) DIENE COMPLEX

PROCESS DESCRIPTION

The crude product from the previous steps of this process, equations 1) to 4) which is still contained in the reactor used is agitated at a pot temperature of 20–25° C. and piperylene concentrate (1,3-pentadiene) is added.

Butylmagnesium chloride in THF is fed into the reactor. The reaction is exothermic. When the Grignard feed is done, the reaction mixture is agitated for an additional ½ hour at a pot temperature of 35–40° C.

This mixture is then distilled atmospherically to a pot temperature of 85° C., cooled to 20–25° C., and then vacuum distilled at ≦65° C. One drum of deoxygenated hydrocarbon solvent and Celite is added at 20–250° C., and the resulting mixture is filtered through the large 33 inch sparkler. The filter cake is hydrolyzed. The resulting solution is then vacuum distilled at ≦65° C.

Six drums of deoxygenated Isopar are charged to the reactor, 2 drums at a time, and then vacuum distilled at ≦650° C. to remove THF and toluene. When the solvent concentrations are appropriate, 1 drum of deoxygenated Isopar and Celite are added. The resulting solution is filtered through a precoated small sparkler filter into a cylinder. The filter cake may be discarded. The reaction is illustrated by the following equation 5).

5)

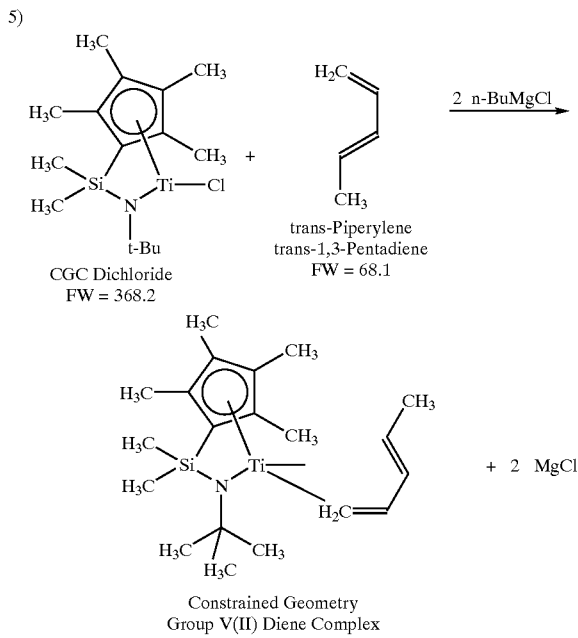

SUMMARY OF THE INVENTION

The invention provides ligands of novel constrained geometry Group 4(II) diene complexes and complexes derived therefrom which have an olefin polymerization activity significantly greater than that demonstrated by known complexes of the same type.

In particular, the invention provides complexes of the formula

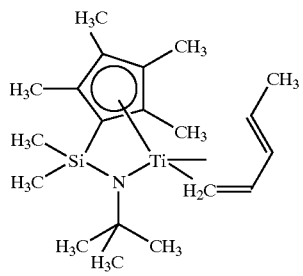

which have an olefin activity substantially in excess of 100%, e.g., at least about 130%, of the aforesaid "standard activity".

Pursuant to one aspect of the invention, a cyclopentadienyl silyl amine is treated with an alkali metal alkyl and thereafter with a dialkyl silyl dihalide to produce cyclopentadienyl silyl amine ligand (CpSA ligand). The ligand is treated with a group 4 metal tetrahalide adduct of a linear ether having at least two oxygen atoms and an alkali metal alkyl to produce a dihalida ligand of the ultimately desired group 4(III) complex having the formula.

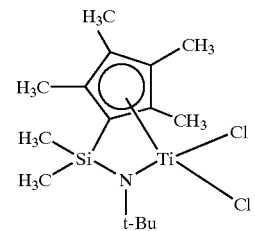

The dihalide ligand is treated with a diene and an alkali metal alkyl used in stoichiometric excess. Dienes useful in the invention are described in U.S. Pat. Nos. 5,470,993 and 6,015,916. The unreacted alkali metal alkyl in the consequent reaction mixture is quenched, for example, by chlorotrimethyl silane. The complex so produced is apparently free or substantially so of impurities which may result in undesirable gel formation and impair single site olefin polymerization functionality.

DETAILED DESCRIPTION OF THE INVENTION

Various group 4 metal tetrachloride-ether adducts are known. See, generally, U.S. Pat. No. 5,470,993 and published German application DE 197 39 946 A1. Each of the adducts described in these references is useful in this invention. The 1,2-dimethoxyethane (DME) adducts are preferred.

One method for preparing a DME group 4 metal tetrahalide adduct is described in U.S. Pat. No. 6,015,916, Col. 4, 11. 61–66. More generally useful adducts are prepared by treating from any compound or formula X—OYO.OX in which X is a $C_1$ to $C_{10}$ alkyl group, and Y is a $C_2$ to $C_{10}$ alkane.

Any group 4 tetrahalideether adduct may be used. Titanium tetrachloride DME adducts are preferred. The adduct is it preferably prepared in a hydrocarbon solvent. The mol ratio of the reactants is preferably about 1:1 with a small excess of the ether reactant.

Any alkali metal alkyl having the formula A—R, in which A may be any alkali metal, preferably lithium, and R is any alkyl group, preferably a $C_1$ to $C_{10}$ alkyl group, may be used. N-butyllithium is preferred.

The synthesis of the dihalo metallocene ligand is conducted in a non-interfering medium. Suitable media include hydrocarbons, preferably a $C_5$ to $C_8$ alkane, and mixtures of an alkane and ethyl ether. The synthesis may be performed at any effective reaction temperature. A preferred temperature range is from −20° C. to 0° C. Tho reaction mixture contains the dihalo ligand in the non-interfering media. Upon cooling, the dihalo ligand separates from the reaction mixture as a crystalline solid which may be removed by filtration under an inert atmosphere, preferably nitrogen. The isolated dihalo ligand may be recrystallized to further reduce impurity content.

The alkali metal alkyl is used in stoichiometric excess to reduce substantially all of the group 4(IV) dihalo ligand to the group 4(II) finished catalyst and to reduce any other group 4(IV) compounds which may be present in the reaction mixture to group 4(II) compounds or other compounds of minimal adverse affect on the activity or single site functionality of the finished catalyst. The excess alkali metal alkyl is quenched, for example, with chlorotrimethyl silane. The product is understood to comprise a single site catalyst composite essentially free of group 4(IV) or group 4(III) compounds and other impurities which may adversely affect single site polymerization activity.

EXEMPLIFICATION OF THE INVENTION

1. Synthesis of the Cyclopentadienyl Silyl Amine Ligand

A cyclopentadienyl compound as defined is charged to a vessel. THF is added, preferably at a temperature from about −20° C. to −10° C., depending upon the cyclopentadienyl compound used. Dimethyldichlorosilane is fed in at a low temperature of about −10° C. to 0° C. The vessel is agitated and the contents warmed to room temperature and eluted thereafter. The selected alkylamine, preferably a $C_1$ to $C_{10}$ alkyl amine, is fed into the vessel at low temperature, e.g., about −10° C. After agitation and warming to room temperature, the vessel is heated, and THF and unreacted amine are removed. A slurry may form. If so, heptane or equivalent hydrocarbon media may be added. The slurry is filtered. The filtrate contains cyclopentadienyl silyl amine ligand (CpSA ligand) of formula:

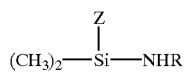

in which Z is a cyclopentadienyl group and R is an alkyl group derived from the alkyl amine reactant.

2. Preparation of the Dihalo Ligand

The dihalo ligand may be synthesized in the manner described in U.S. Pat. No. 6,015,916, Col. 3, 1. 60, part (2). In general, the cyclopentadienyl silyl amine may be treated with an unreduced group 4 tetrachloride, preferably in the form of a DME or equivalent adduct in a hydrocarbon solvent. The Ti(IV) of the dihalo intermediate is converted to Ti(II) in the final complex by treatment with an alkali metal alkyl as described, preferably butyllithium, and a diene in a non-interfering, preferably hydrocarbon, medium at a preferred temperature of −10° C. to 0° C. The alkali metal alkyl is used in stoichiometric excess to reduce the group 4(IV) ligand to the group 4(II) finished catalyst and to reduce any other group 4(IV) compounds which may be present in the reaction mixture. The excess alkali metal alkyl is quenched, preferably with chlorotrimethylsilane.

EXAMPLES DEMONSTRATING ENHANCED POLYMERIZATION ACTIVITY

EXAMPLE 1

All apparatus used in this example were clean, dry and nitrogen-purged. Presence of THF was precluded.

21.2 kg of ethyl ether and 6.5 kg of CPSA ligand (assumed 95% purity) were charged into a first reactor. The pot temperature was reduced to −20° C.

21.2 kg of 15% n-butyllithium in hexane was slowly added with the pot temperature maintained between −20° C. and −10° C. After the feed was completed, the pot temperature was raised to 20° C. over 1 hour, and the pot contents were agitated for 4 hours at 20–25° C. A reaction mixture containing a CpSA dllithio salt was produced.

20 34.2 kg of deoxygenated heptane and 2.6 kg of dimethoxyethane were charged into a second reactor. The pot temperature was adjusted to about 10–15° C.

4.8 kg of titanium tetrachloride were charged to the second reactor at a pot temperature of between 15° C. and 30° C. Upon completion of the feed, the speed of agitation of the second reactor contents was increased. Agitation continued for about 3 hours at a pot temperature of 20–25° C.

The pot temperature of each of the first and second reactors was adjusted to 15–20° C. Thereafter, the contents of the first reactor were transferred to the second reactor with the pot temperature of the second reactor maintained at 20–25° C. The second reactor contents were then agitated for about 12 hours at 25–28° C.

A reaction mixture containing the dichloride ligand having the formula set forth on page 13 hereof was produced in the second reactor. After solvent stripping, 47.0 kg of deoxygenated heptane was added to the second reactor. The second reactor pot temperature was adjusted to −15° C. Thereafter, 6 kg of piperylene was charged to the second reactor. 23.3 kg of 6M butyllithium in hexane were fed into the second reactor. During this feed, the pot temperature was maintained between −15° C. and −10° C. Upon completion of the food, the pot temperature was adjusted to 20–25° C. over 1 hour. The reaction mixture was agitated for about three hours at 20–25° C.

1.5 kg of trimethylsilicon chloride (TMSCl) was added. The pot temperature was adjusted to 40–45° C. with agitation for 2 hours. Thereafter, the pot temperature was adjusted to 20–25° C. and the reaction mixture was filtered. The cake was rinsed with deoxygenated heptane Theory yield—9.1 Kg contained Actual yield—7.454 Kg contained.

Activity (determined as described above)—170%.

EXAMPLE 2

All apparatus used in this example were clean, dry and nitrogen-purged. Presence of THF was precluded.

8.5 kg of ethyl ether and 2.6 kg of CpSA ligand (95% purity assumed) were charged into a clean, Isopar-rinsed, nitrogen-purged first reactor. The pot temperature was −20° C.

13.7 kg of deoxygenated Isopar E and 1.0 kg of dimethoxymethane were charged into a dry, nitrogen-purged second reactor. The pot temperature was adjusted to 10–15° C.

1.9 kg of titanium tetrdchloride were fed into the second reactor with slow agitation of the reactor contents and with the pot temperature maintained between 15° C. and 30° C. Upon completion of the feed, the agitation was increased, and the contents of the second reactor were agitated for about 3 hours at 20–25° C.

The pot temperature of each of the first and second reactors was adjusted to 15–20° C. The agitated contents of the first reactor were transferred to the second reactor with the second reactor pot temperature maintained at 20–25° C. The contents of the second reactor were agitated for about 12 hours at 20–28° C. The reaction mixture in the second reactor contained the dichloride ligand set forth on page 13 hereof. Solvents were stripped from the reaction mixture.

The pot temperature of the second reactor was adjusted to 15° C. 2.0 kg of piperylene were charged to the reactor, 8.5 kg of 15% butyllithium in hexane were slowly fed into the second reactor temperature maintained between −15° C. and −10° C. After the feed was completed, the pot temperature was adjusted to 20–25° C. over a 1 hour time period. The reaction mixture was agitated for 3 hours at 20–25° C.

600 g of TMSCl were added, and the reaction mixture was agitated for 1 hour. The reaction mixture which contained the desired group 4(II) diene complex was filtered, and the cake was rinsed with deoxygenated Isopar.

Theory yield (contained)–3.65 kin

Actual yield (contained)–2.59 (71% yield)

Activity (as determined in the manner described above)–140%.

EXAMPLES 3 AND 4

Synthesis procedures substantially as described in Examples 1 and 2 yielded Group 4(II) diene complex products having activities, when determined as described above, of 165% and 130%.

We claim:

1. A method for preparing a compound having the formula:

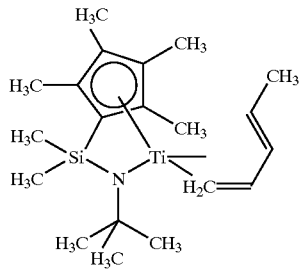

which comprises:

(i) providing a first reactor containing the reaction product of a cyclopentadienyl silyl amine and an alkali metal alkyl, (ii) providing a second reactor containing the adduct of formula $MX_4$—DME wherein M is a group 4 element, X is a halogen, and DME is dimethoxyethane, (iii) adjusting the pot temperature of each of said first reactor and said second reactor to be within the ranges of about 20–30° C., (iv) thereafter combining the contents of the first reactor with the contents of the second reactor wherein a reaction mixture is produced in said second reactor, and wherein said reaction mixture produced in said second reactor contains a compound of the formula

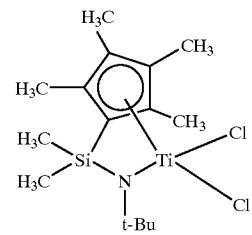

(v) distilling solvents from said reaction mixture containing said compound in said second reactor, and (vi) converting said step (iv) compound to a compound of the formula

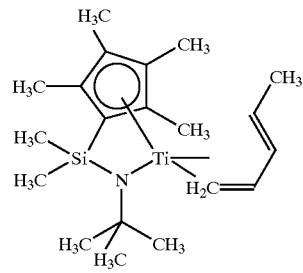

* * * * *